United States Patent [19]
Hemmerich et al.

[11] Patent Number: 5,147,309
[45] Date of Patent: Sep. 15, 1992

[54] APPARATUS FOR PRIMING A HYPODERMIC NEEDLE WITH HAZARDOUS FLUID

[75] Inventors: Karl J. Hemmerich, Del Mar; Henry D. Kraus, Valley Center, both of Calif.

[73] Assignee: Biosafety Systems, Inc., San Diego, Calif.

[21] Appl. No.: 780,925

[22] Filed: Oct. 22, 1991

[51] Int. Cl.$^5$ .............................................. A61M 1/00
[52] U.S. Cl. .................................. 604/122; 604/192; 604/263
[58] Field of Search ............... 604/126, 122, 192, 197, 604/198, 263, 415, 272

[56] References Cited

U.S. PATENT DOCUMENTS

| | | | |
|---|---|---|---|
| 3,073,307 | 1/1963 | Stevens | 604/192 |
| 4,085,737 | 4/1978 | Bordow | 604/263 |
| 4,240,425 | 12/1980 | Akhavi | 604/199 |
| 4,249,530 | 2/1981 | Millet | 604/192 |
| 4,735,311 | 4/1988 | Lowe et al. | 206/365 |
| 4,769,026 | 9/1988 | Strung | 604/263 |
| 4,775,376 | 10/1988 | Strung | 604/415 |
| 4,892,521 | 1/1990 | Laico et al. | 604/192 |
| 4,950,242 | 8/1990 | Alvarez | 604/110 |
| 4,986,818 | 1/1991 | Imbert et al. | 604/192 |

FOREIGN PATENT DOCUMENTS 3842317 1/1990 Fed. Rep. of Germany .

Primary Examiner—John G. Weiss
Assistant Examiner—Michael Lynch
Attorney, Agent, or Firm—Fulwider, Patton, Lee & Utecht

[57] ABSTRACT

The apparatus for priming a hypodermic needle with hazardous fluid and for retaining the hazardous fluid expelled from the needle in purging air from the needle includes a hypodermic needle and a tubular sheath member with a distal fluid containment chamber. The proximal end of the needle is adapted to be connected to a syringe or I.V. tubing, and is preferably removably mounted in the base portion of the sheath. The containment chamber includes a sealing membrane through which the needle extends, and a vent with a hydrophobic filter is disposed in the distal end of the containment chamber for venting air. A deflector shield is also provided within the containment chamber between the hydrophobic filter at the vent opening and the hypodermic needle for deflecting the hazardous fluid expelled from the distal end of the needle. The deflector shield preferably includes a planar member extending transversely within the containment chamber with a shield portion adjacent to the needle, and at least one fluid flow passage for communicating air from the needle through the vent.

7 Claims, 2 Drawing Sheets

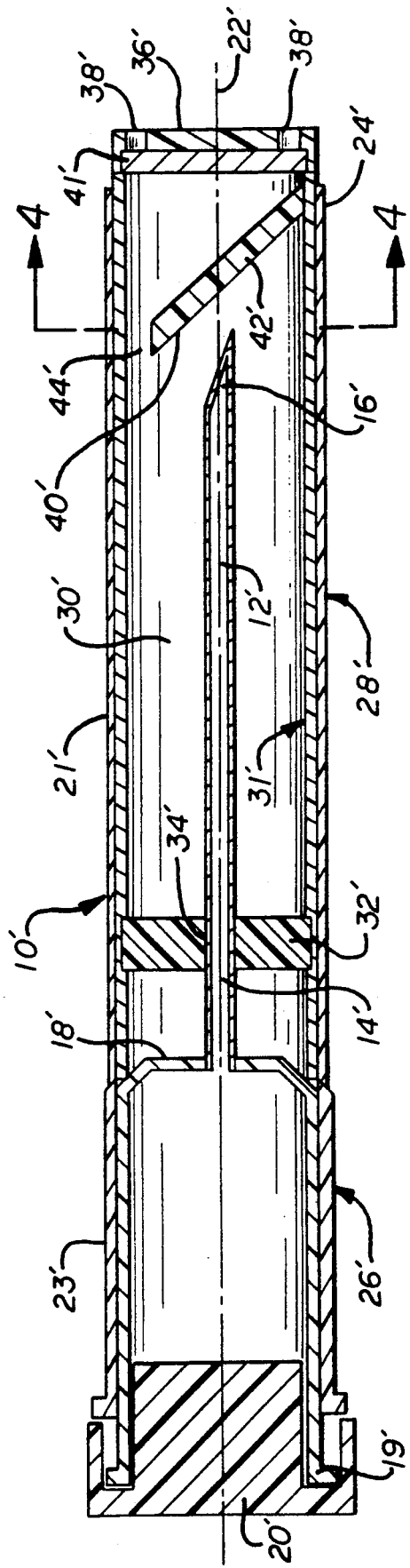
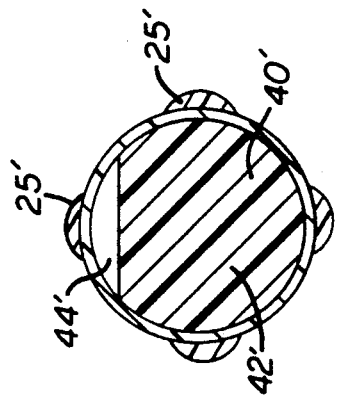
FIG. 3
FIG. 4

APPARATUS FOR PRIMING A HYPODERMIC NEEDLE WITH HAZARDOUS FLUID

BACKGROUND OF THE INVENTION

1. Field of the Invention

This invention relates generally to hypodermic needles for injecting medicines intramuscularly, intravenously or into intravenous administration systems, and more particularly relates to apparatus for retaining hazardous fluid, such as chemotherapy agents, ejected in priming such a needle by purging air from the needle.

2. Description of Related Art

Current practice in preparing hypodermic syringes for injecting fluid medicines into the body of a patient typically involves priming the hypodermic needle by purging air from the needle and ejecting a small portion of the fluid from the needle of the syringe to insure that air has been removed from the syringe and the needle, to avoid causing an air embolism in the patient. The fluid is typically squirted into the air or onto an absorbant material, but in cases where the fluid is hazardous to the medical personnel preparing the injection, the fluid is commonly ejected into an appropriate waste container, which may result in accidental spattering of the fluid out of the waste container where it can be dangerous.

Another approach to purging air from a hypodermic needle by ejecting the air and a portion of a hazardous fluid from a hypodermic needle involves ejecting the air and fluid into a specially sealed needle guard sheath designed to retain the fluid. One such needle guard sheath includes a pad of absorbent material for absorbing the hazardous fluid, and an agent such as bleach in the absorbent pad for neutralizing the hazardous fluid. A buildup of pressure in such a sealed sheath can prevent effective purging of the syringe needle if the amount of air and fluid that must be purged to prime the syringe needle exceeds the capacity of the sheath. An absorbent pad or filter can to some extent prevent the escape of hazardous fluid from a vented purging sheath, but it has been found that the spray of fluid from the needle can also penetrate such a pad if the force of the spray is sufficient. One such needle guard sheath includes a vent with a hydrophobic filter to retain fluid while allowing the flow of air through the filter. It has been found that the flow of air through such a hydrophobic filter can also be blocked by an accumulation of the spray of fluid on the filter, allowing pressure buildup within the sheath to interfere with effective purging of air in priming the syringe needle. It would therefore be desirable to provide a sheath for a hypodermic needle which would vent air purged from the needle, but which would retain any hazardous fluid also ejected from the needle, and which would avoid blockage of an air vent by the fluid.

Conventional needle guard sheaths frequently also allow technicians to accidentally stick themselves with the hypodermic needle in placing the sheath over the needle. A flange at the base of the sheath can help to protect the hands of the technician from the needle to some extent, but it would be desirable to provide a needle guard sheath removably mounted on a hypodermic needle, adapted to be connected to a syringe or I.V. administration set used for supplying hazardous fluid to be administered through the needle, so that the needle can be connected to the syringe or I.V. administration set, purged of air and primed, without risk of needle sticks to the technician.

SUMMARY OF THE INVENTION

The present invention thus provides for an improved apparatus for purging air from a hypodermic needle adapted to be connected to a syringe or intravenous administration system, and for priming the needle with hazardous fluid. The apparatus includes a needle guard sheath portion and a needle removably joined together as a unit which can be attached to a syringe or I.V. administration set. The sheath includes a containment chamber vented at the distal end of the sheath, which retains the hazardous fluid as it is purged from the needle, and which releases air pressure from the chamber. A hydrophobic, gas permeable filter is disposed in the distal end of the chamber to prevent fluid from passing through the vent openings. A deflector member positioned in the containment chamber between the needle and the filter deflects the spray of hazardous fluid away from the filter to allow venting of air from the sheath without blockage of the filter by the hazardous fluid.

Briefly, and in general terms, the apparatus for priming a hypodermic needle with hazardous fluid and for retaining the hazardous fluid expelled from the needle comprises a hypodermic needle and a tubular sheath member having a proximal base portion and a distal fluid containment portion. The proximal end of the needle includes a tubular connector adapted to be connected to a source of the hazardous fluid, such as a syringe or I.V. tubing. The tubular connector portion of the needle is preferably removably mounted in the proximal base portion of the sheath, with the needle disposed coaxially within the containment portion. Sealing means are preferably disposed within the containment portion for preventing escape of the hazardous fluid from the proximal end of the tubular sheath member; and means are disposed in the containment portion for venting air expelled from the needle from the containment portion while preventing escape of the hazardous fluid from the containment portion through the distal end of the tubular sheath member.

The means for venting preferably comprises a gas permeable hydrophobic filter and one or more vent openings at the distal end of the sheath member. Venting of the containment chamber releases the buildup of pressure which can occur as the needle is purged, eliminating any pressure gradient between the containment chamber and the atmosphere, to avoid squirting of the needle which can otherwise occur with unvented enclosures upon removal from the sheath. Deflector means are also preferably provided within the containment chamber between the means for venting and the hypodermic needle for deflecting the hazardous fluid expelled from the distal end of the needle away the means for venting. The deflector means preferably comprises a planar member extending transversely within the portion having a shield portion adjacent to the needle end for deflecting hazardous fluid expelled from the needle away from the means for venting and at least one fluid flow passage for communicating air from the needle through the means for venting.

In one preferred embodiment, the deflector means is a generally circular planar member, and the shield portion is located in a central portion of the member, with a plurality of spaced apart apertures disposed radially about the shield portion. In an alternate embodiment, the deflector means may comprise a planar member extending at an oblique angle to the axis of the sheath member and the needle having a shield portion adjacent to the needle distal end for deflecting hazardous fluid expelled from the needle away from the means for venting, and defining at least one fluid flow passage for communicating air expelled from the needle through the means for venting. The deflector operates to prevent breakthrough of the hazardous fluid through the filter and vent structures provided at the end of the sheath, due to high pressure hammer of the spray of fluid which can be ejected from the needle in purging the source of hazardous fluid and the needle of air. The sealing means currently also preferably comprises an elastomeric piercing membrane through which the needle extends, so that the piercing membrane will clean the surface of the needle of the hazardous fluid when the needle is withdrawn from the piercing membrane. The containment portion of the tubular sheath member may also have its inner surface coated with a dye indicator material for indicating the presence of the hazardous fluid in the containment portion.

These and other aspects and advantages of the invention will become apparent from the following detailed description, and the accompanying drawing, which illustrates by way of example the features of the invention.

BRIEF DESCRIPTION OF THE DRAWINGS

FIG. 3 is a longitudinal sectional view of an alternate embodiment of the hypodermic needle priming apparatus of the invention; and FIG. 4 is a cross-sectional view of the tubular sheath member of the apparatus taken along line 4—4 of FIG. 3.

DETAILED DESCRIPTION OF THE PREFERRED EMBODIMENTS

Common methods of priming a hypodermic needle for use in administering a hazardous fluid such as chemotherapy drugs or other cytotoxic fluids are frequently ineffective in protecting the health care workers preparing the needle from the dangers of contamination by the hazardous fluid. Purging the fluid from the needle in a sealed purging sheath can prevent effective purging of the syringe needle unless the sheath is vented, but venting of the fluid containment area of the sheath can also allow for escape of the hazardous fluid. Absorbant pads can be penetrated by the spray of fluid from the needle if the force of the spray is sufficient, and a hydrophobic filter designed for retaining the fluid can be blocked by the spray of fluid on the filter, allowing pressure buildup within the purging device to interfere with effective priming of the syringe needle. Flanges on a needle sheath are also not completely effective in protecting technicians from accidental needle punctures. The invention therefore provides a combination needle and vented purging sheath having a deflector shield for deflecting the spray of fluid from the hypodermic needle as it is purged of air, without risk of contamination or injury to the health care worker.

Figure 1:
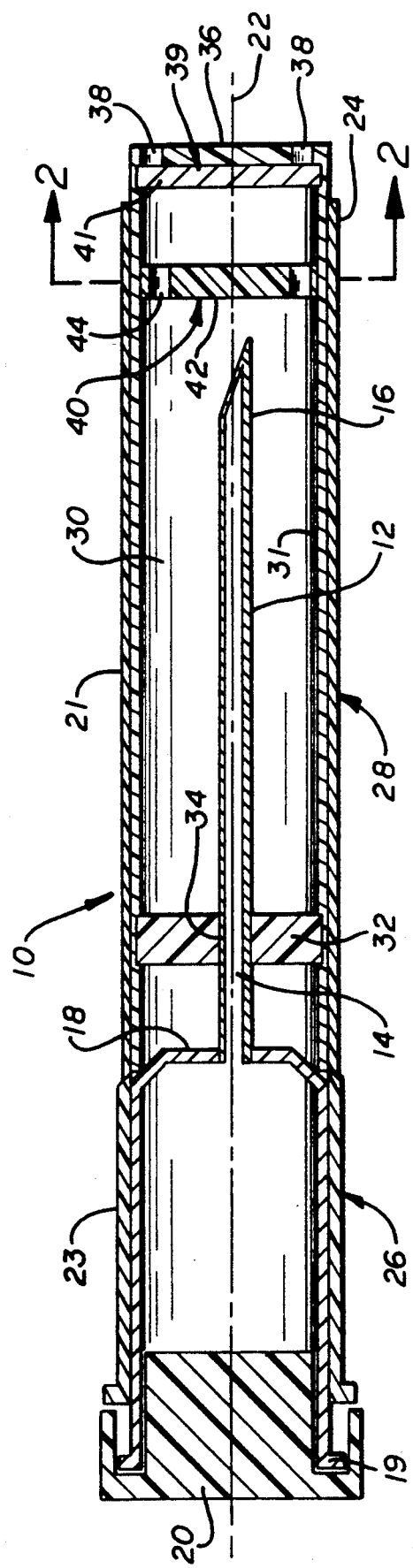
FIG. 1 is a longitudinal sectional view of the hypodermic needle priming apparatus of the invention.
Figure 2:
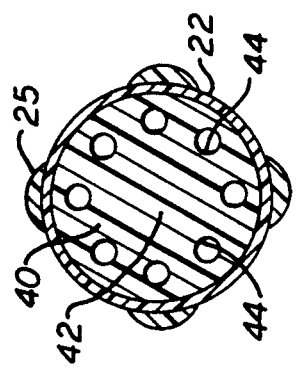
FIG. 2 is a cross-sectional view of the tubular sheath member of the apparatus of the invention taken along line 2—2 of FIG. 1.

As is illustrated in the drawings, the invention is accordingly embodied in an apparatus 10 for priming a hypodermic needle with hazardous fluid from a source of supply (not shown) of the hazardous fluid, such as a syringe or an intravenous administration set, and for retaining the hazardous fluid expelled from the needle. As is shown in FIGS. 1 and 2, in one preferred embodiment the apparatus includes a hypodermic needle 12 having a proximal end 14 and a distal end 16, and a tubular connector 18 on the proximal end of the needle adapted to be connected to the source of the hazardous fluid for purging of air and a small amount of the hazardous fluid, both of which are expelled from the distal end of needle. A removable protector cap 20 may be provided over the open distal end 19 of the connector, to keep the connector and needle sanitary until the connector is to be fitted to the source of supply of the hazardous fluid. The needle is coaxially disposed within a tubular sheath member 21 having a longitudinal axis 22, a proximal end 23 and a distal end 24, a proximal base portion 26 and a distal fluid containment portion 28 having an inner containment chamber 30 where the needle resides, with the tubular connector removably disposed in the proximal base portion. The sheath member is currently preferably injection molded from polypropylene, although other like materials may be suitable, and may be provided with external ribs 25 to provide increased structural strength and rigidity, and to facilitate convenient gripping of the sheath member by hand. The inner surface 31 of the containment chamber may also be advantageously coated with a dye indicator material, such as Mallincrott dye, which changes color upon exposure to the hazardous fluid, to indicate the presence of the hazardous fluid in the containment chamber.

The needle also preferably extends through a sealing means such as a resilient elastomeric septum 32 or piercing membrane, which is preferably disposed within the containment portion of the sheath, for preventing escape of the hazardous fluid from the proximal end of the tubular sheath member. The piercing membrane is preferably formed from latex, although other such materials may also be suitable. The piercing membrane can be mechanically snap inserted into a recess in the containment chamber of the sheath member, or can alternatively be heat bonded, or bonded with adhesive, such as with a cyanoacrylate adhesive available from Loctite Corporation. When the hazardous fluid is expelled from the needle, the fluid spray may be deflected back upon, or drip onto, and collect on the exterior surface of the needle. Thus, when the needle is withdrawn through the opening 34 in the piercing membrane of the sheath prior to use, the piercing membrane operates to clean the surface of the needle of the hazardous fluid as the needle is withdrawn through the resilient piercing membrane. The sheath member containing the purged hazardous fluid can then be disposed of in an appropriate waste container, without danger of contamination from the hazardous fluid.

A distal end wall 36 of the containment portion of the sheath preferably includes one or more vents 38 for venting air from the containment chamber which is expelled from the needle. The vents allow release of pressure from the containment chamber as the needle is purged, and maintain a zero pressure gradient between the containment chamber and the atmosphere, to avoid squirting of the needle which can otherwise occur with unvented enclosures upon removal from the sheath. A gas permeable hydrophobic filter 39 is preferably disposed in the containment portion between the vent openings 38 and a deflector member 40 for preventing escape of the hazardous fluid from the containment portion through the distal end of the tubular sheath member. The hydrophobic filter may include a disclike housing 41 fitted within the containment chamber, either snap fitted in a recess or bonded by adhesive or heat bonding to the sheath member. Alternatively, the hydrophobic filter may be disposed in the one or more vent openings themselves, at the distal end of the sheath. Gas permeable hydrophobic filter material is available commercially from several suppliers. The deflector member and sheath member are both currently preferably formed of polypropylene, although other like materials may also be suitable. The deflector member can be mounted with the containment chamber by a mechanical snap fit, or adhesive or heat bonding. The deflector member is preferably disposed between the distal end of the hypodermic needle and the vent, extending transversely within the containment portion for deflecting the fluid expelled from the distal end of the needle away from the vent.

The deflector member currently preferably is provided in the form of a planar member having a shield portion 42 adjacent to the needle end for deflecting hazardous fluid expelled from the needle away from the means for venting, and is provided with at least one fluid flow passage 44 for communicating air from the needle through the distal vent openings. In one preferred embodiment, the deflector member is generally circular and includes a centrally located shield area, with a plurality of spaced apart apertures 44 disposed radially about the shield portion.

A second preferred embodiment illustrated in FIGS. 3 and 4 is nearly identical to the first embodiment, and like structures are identified with like reference numerals. Thus, in the second embodiment, the apparatus 10' for priming a hypodermic needle with hazardous fluid and for retaining the hazardous fluid expelled from the needle includes a hypodermic needle 12' having a proximal end 14' and a distal end 16', and a tubular connector 18' on the proximal end of the needle for connecting the needle to a syringe or I.V. administration set containing hazardous fluid. A removable protector cap 20' may be provided over the open distal end 19' of the connector. The needle is coaxially disposed within a tubular sheath member 21' having a longitudinal axis 22', a proximal end 23' and a distal end 24', a proximal base portion 26' and a distal fluid containment portion 28' having an inner containment chamber 30' where the needle resides, with the tubular connector of the hypodermic needle removably disposed in the proximal base portion of the needle guard sheath member. The sheath member may also be provided with external ribs 25'. The inner surface 31' of the containment chamber may also be advantageously coated with a dye indicator material, such as Mallincrott dye, which changes color upon exposure to the hazardous fluid, to indicate the presence of the hazardous fluid in the containment chamber.

The containment chamber also includes a sealing means such as a resilient elastomeric septum 32' or piercing membrane, with an opening 34' through which the needle extends, for preventing escape of the hazardous fluid from the proximal end of the tubular sheath member and for cleaning the surface of the needle of the hazardous fluid as the needle is withdrawn through the resilient piercing membrane.

A distal end wall 36' of the containment portion of the sheath preferably includes one or more vents 38' for venting air from the containment chamber which is expelled from the needle, and a gas permeable hydrophobic filter 39' is preferably disposed in the containment portion between the vent openings 38' and a deflector member 40' for preventing escape of the hazardous fluid from the containment portion through the distal end of the tubular sheath member. The hydrophobic filter may include a disclike housing 41' fitted within the containment chamber, either snap fitted in a recess or bonded by adhesive or heat bonding to the sheath member. In the second preferred embodiment, the deflector member 40' is a planar member extending at an oblique angle to the axis of the sheath, with a shield portion 42' adjacent to the needle distal end for deflecting hazardous fluid expelled from the needle away from the vent. A fluid flow passage 44' is provided, typically at the most proximal extremity of the obliquely disposed deflector member, to allow air expelled from the needle to escape through the vent, while the fluid is deflected and trapped by the deflector shield member.

From the foregoing, it can thus be seen that the invention permits priming a hypodermic needle for a syringe or an I.V. administration set with hazardous fluid, with the sheath portion and needle together as a unit operating to avoid contamination from purging the needle and syringe or I.V. set of air. The sheath retains the hazardous fluid as it is purged from the needle, and a hydrophobic filter and vent allow release of air pressure from the chamber, eliminating buildup of any pressure gradient between the containment chamber and the atmosphere, to avoid squirting of the needle. A deflector member is provided to deflect the spray of hazardous fluid away from the filter to allow venting of air from the sheath without blockage of the filter by the hazardous fluid. It should be apparent that other forms of the transverse deflector member may also be suitable, such as a truncated circular planar member disposed at a right angles to the axis of the needle guard sheath, with the truncated portion of the deflector member allowing the flow of purged air to the filter and vent structures. The deflector member could also take the form of a planar member or other type of deflector structure suspended in the containment chamber so that air and hazardous fluid would be deflected, to prevent high pressure hammer of the fluid through the filter and vent structures.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An apparatus for purging air from a hypodermic needle and priming the needle with hazardous fluid, and for retaining said hazardous fluid expelled from said needle, comprising:

a) a hypodermic needle having proximal and distal ends and a tubular connector on said proximal end of said needle adapted to be connected to a source of said hazardous fluid for communication of air and said hazardous fluid from said source to be expelled through said distal ends of said needle;

b) a tubular sheath member having a longitudinal axis, proximal and distal ends, a proximal base portion and a distal fluid containment portion, said tubular connector being removably disposed in said proximal base portion, and said needle being disposed coaxially within said containment portion;

c) means disposed within said containment portion for preventing escape of said hazardous fluid from said proximal end of said tubular sheath member;

d) means disposed in said containment portion for venting air expelled from said needle from said containment portion and for preventing escape of said hazardous fluid from said containment portion through said distal end of said tubular sheath member; and e) a planar deflector member within said containment portion between said distal end of said hypodermic needle and said means for venting for deflecting said fluid expelled from said distal end of said needle away from said means for venting, said planar deflector member extending transversely within said containment portion, having a shield portion adjacent to said needle end for deflecting hazardous fluid expelled from said needle away from said means for venting, and having at least one fluid flow passage for communicating air from said needle through said means for venting.

2. The apparatus of claim 1, wherein said deflector member is generally circular and said shield portion is located centrally therein, and wherein said deflector member includes a plurality of spaced apart apertures disposed radially about said shield portion.

3. The apparatus of claim 1, wherein said deflector member extends at an oblique angle to said axis of said sheath member.

4. The apparatus of claim 1, wherein said means for venting comprises a gas permeable hydrophobic filter.

5. The apparatus of claim 1, wherein said needle has an exterior surface upon which said hazardous fluid can collect when said fluid is expelled from said needle, and said sealing means comprises a piercing membrane through which said needle extends, whereby said piercing membrane can clean the surface of said needle of said hazardous fluid when said needle is withdrawn from said piercing membrane.

6. The apparatus of claim 1, wherein said proximal base portion of said sheath member has an open proximal end and includes a removable protector cap over said base portion proximal end.

7. An apparatus for purging air from a hypodermic needle and priming the needle with hazardous fluid, and for retaining said hazardous fluid expelled from said needle, comprising:

a) a hypodermic needle having proximal and distal ends and a tubular connector on said proximal end of said needle adapted to be connected to a source of said hazardous fluid for communication of air and said hazardous fluid from said source to be expelled through said distal ends of said needle;

b) a tubular sheath member having a longitudinal axis, proximal and distal ends, a proximal base portion and a distal fluid containment portion, said containment portion having an inner surface coated with a dye indicator material for indicating the presence of said hazardous fluid in said containment portion, said tubular connector being removably disposed in said proximal base portion, and said needle being disposed coaxially within said containment portion;

c) sealing means disposed within said containment portion for preventing escape of said hazardous fluid from said proximal end of said tubular sheath member;

d) means disposed in said containment portion for venting air expelled from said needle from said containment portion and for preventing escape of said hazardous fluid from said containment portion through said distal end of said tubular sheath member; and e) deflector means within said containment portion between said distal end of said hypodermic needle and said means for venting for deflecting said fluid expelled from said distal end of said needle away said means for venting.

* * * * *